US00PP20078P2

(12) United States Plant Patent
Takao

(10) Patent No.: US PP20,078 P2
(45) Date of Patent: Jun. 9, 2009

(54) ***LITHODORA* PLANT NAMED 'WHITE STAR'**

(50) Latin Name: *Lithodora diffusa*
Varietal Denomination: White Star

(76) Inventor: Danny Takao, Takao Nursery, 2665 N. Polk Ave., Fresno, CA (US) 93722

( * ) Notice: Subject to any disclaimer, the term of this patent is extended or adjusted under 35 U.S.C. 154(b) by 0 days.

(21) Appl. No.: 12/154,225

(22) Filed: May 21, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Lithodora* plant named 'White Star', characterized by its compact, upright, outwardly spreading and uniformly mounded plant habit; freely branching habit; dark green-colored leaves; numerous blue and white bi-colored flowers; and good garden performance.

1 Drawing Sheet

Botanical designation: *Lithodora diffusa.*
Cultivar denomination: 'White Star'.

BACKGROUND OF THE INVENTION

The present invention relates to a new and distinct cultivar of *Lithodora,* botanically known as *Lithodora diffusa* and hereinafter referred to by the name 'White Star'.

The new *Lithodora* is a naturally-occurring branch mutation of *Lithodora diffusa* 'Grace Ward', not patented. The new *Lithodora* was discovered and selected by the Inventor on a single flowering plant of 'Grace Ward' within a population of plants of 'Grace Ward' in a controlled greenhouse environment in Sacramento, Calif. in March, 2004.

Asexual reproduction of the new *Lithodora* by vegetative cuttings in a controlled greenhouse environment in Lancaster, Pa. since Jun. 14, 2004, has shown that the unique features of this new *Lithodora* are stable and reproduced true to type in successive generations.

SUMMARY OF THE INVENTION

The new *Lithodora* has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'White Star'. These characteristics in combination distinguish 'White Star' as a new and distinct cultivar of *Lithodora:*

1. Compact, upright, outwardly spreading and uniformly mounded plant habit.
2. Freely branching habit.
3. Dark green-colored leaves.
4. Numerous blue and white bi-colored flowers.
5. Good garden performance.

Plants of the new *Lithodora* differ from plants of the parent, 'Grace Ward', primarily in flower color as plants of 'Grace Ward' have blue-colored flowers.

Plants of the new *Lithodora* can be compared to plants of the *Lithodora* 'Lithospermum Star', disclosed in U.S. Plant Pat. No. 10,096. In side-by-side comparisons conducted in Lancaster, Pa., plants of the new *Lithodora* differed from plants of 'Lithospermum Star' in the following characteristics:

1. Plants of the new *Lithodora* and 'Lithospermum Star' differed in flower color as plants of 'Lithospermum Star' had flowers with blue-colored centers and white-colored margins.
2. Plants of the new *Lithodora* had shorter peduncles than plants of 'Lithospermum Star'.

BRIEF DESCRIPTION OF THE PHOTOGRAPHS

The accompanying colored photographs illustrate the overall appearance of the new *Lithodora,* showing the colors as true as it is reasonably possible to obtain in colored reproductions of this type. Colors in the photographs may differ slightly from the color values cited in the detailed botanical description which accurately describe the colors of the new *Lithodora.*

The photograph at the bottom of the sheet comprises a side perspective view of a typical plant of 'White Star' grown in a container.

The photograph at the top of the sheet is a close-up view of a typical flower of 'White Star'.

DETAILED BOTANICAL DESCRIPTION

The aforementioned photographs and following observations, measurements and values describe plants grown during the spring in Lancaster, Pa. in 10-cm containers in a polyethylene-covered greenhouse and under conditions which closely approximate commercial *Lithodora* production. During the production of the plants, day temperatures ranged from 18° C. to 29° C. and night temperatures averaged 18° C. Plants were nine months old when the photographs and the description were taken. In the description, color references are made to The Royal Horticultural Society Colour Chart, 1995 Edition, except where general terms of ordinary dictionary significance are used.

Botanical classification: *Lithodora diffusa* 'White Star'.

Parentage: Naturally-occurring branch mutation of *Lithodora diffusa* 'Grace Ward', not patented.

Propagation:

*Type.*—By vegetative cuttings.

*Time to initiate roots, summer.*—About 7 days at 24° C. to 27° C.

*Time to initiate roots, winter.*—About 10 to 12 days at 21° C.

*Time to produce a rooted young plant, summer.*—About 28 to 30 days at 24° C. to 27° C.

*Time to produce a rooted young plant, winter.*—About 32 to 35 days at 21° C.

*Root description.*—Fine, fibrous; white in color.

*Rooting habit.*—Freely branching; moderately dense.

Plant description:

*Plant form/habit.*—Herbaceous perennial. Compact, upright, outwardly spreading and uniformly mounded plant habit. Freely branching habit; when pinched, about 15 primary lateral branches develop. Vigorous growth habit.

*Plant height.*—About 16 cm.

*Plant width (spread).*—About 18 cm by 25 cm.

*Lateral branches.*—Length: About 15 cm. Diameter: About 2.5 mm. Internode length: About 6 mm. Strength: Strong. Texture: Pubescent, bristly. Color: Close to 145C.

Foliage description:

*Arrangement.*—Alternate, simple; sessile.

*Length.*—About 2.5 cm.

*Width.*—About 6 mm.

*Shape.*—Lanceolate.

*Apex.*—Broadly acute.

*Base.*—Truncate.

*Margin.*—Entire.

*Texture, upper and lower surfaces.*—Pubescent, bristly; coarse.

*Venation pattern.*—Pinnate.

*Color.*—Developing leaves, upper surface: Close to 146A. Developing leaves, lower surface: Close to 146B. Fully expanded leaves, upper surface: Close to 147A; venation, close to 147A. Fully expanded leaves, lower surface: Close to 147B; venation, close to 147B.

Flower description:

*Flower type/habit.*—Single tubular flowers with usually three to four flowers and flower buds per lateral branch; about 22 flowers per plant; flowers face upright and outwardly. Flowers are sessile.

*Fragrance.*—None detected.

*Natural flowering season.*—Plants flower continuously during the spring in Lancaster, Pa.

*Postproduction longevity.*—Flowers last about five days on the plant; flowers persistent.

*Flower buds.*—Height: About 1.3 cm. Diameter: About 3 mm. Shape: Lanceolate. Color: Close to 157C.

*Flower diameter.*—About 7 mm.

*Flower length.*—About 1.5 cm.

*Petals.*—Quantity per flower: Typically five fused at the base in a short tube. Lobe length: About 6 mm. Lobe width: About 4 mm. Lobe shape: Roughly oblong. Lobe apex: Rounded. Margin: Entire. Texture, upper and lower surfaces: Sparsely pubescent. Color: When opening, upper surface: Centers, close to 155D; towards the margins, close to 101B. When opening, lower surface: Close to 157C. Fully opened, upper surface: Centers, close to 155D; towards the margins, close to 101A. Fully opened, lower surface: Close to 157B to 157C. Throat: Close to 155D.

*Tube.*—Close to 155D.

*Sepals.*—Quantity per flower: Typically five in a single whorl fused at the base. Length: About 7 mm. Width: Less than 1 mm. Shape: Lanceolate to acicular. Apex: Acute. Margin: Entire. Texture, upper and lower surfaces: Sparsely pubescent. Color, upper and lower surfaces: Close to 145A.

*Reproductive organs.*—Stamens: Quantity per flower: Typically five. Filament length: About 2 mm. Filament color: Close to 155D. Anther shape: Oval. Anther length: About 1 mm. Anther color: Close to 162C. Pollen amount: Sparse. Pollen color: Close to 162D. Pistils: Quantity per flower: One. Pistil length: About 1.2 cm. Stigma shape: Bi-parted. Stigma color: Close to 145C. Style length: About 1 cm. Style color: Close to 145D. Ovary color: Close to 145A.

*Fruits/seeds.*—Fruit and seed development have not been observed on plants of the new *Lithodora.*

Disease/pest resistance: Plants of the new *Lithodora* have not been noted to be resistant to pathogens and pests common to *Lithodora.*

Garden performance: Plants of the new *Lithodora* have been observed to have good garden performance and tolerate rain, wind and temperatures ranging from about −12° C. to about 38° C.

It is claimed:

1. A new and distinct *Lithodora* plant named 'White Star' as illustrated and described.

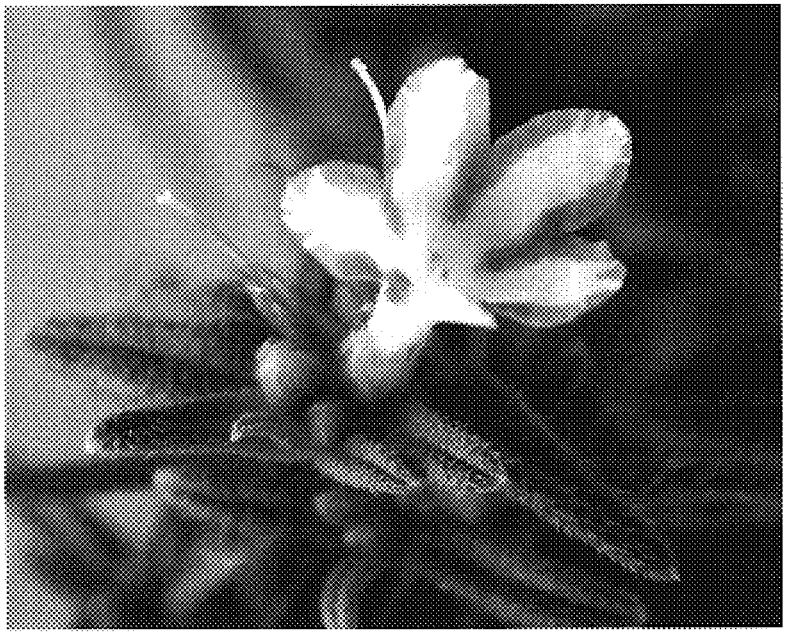
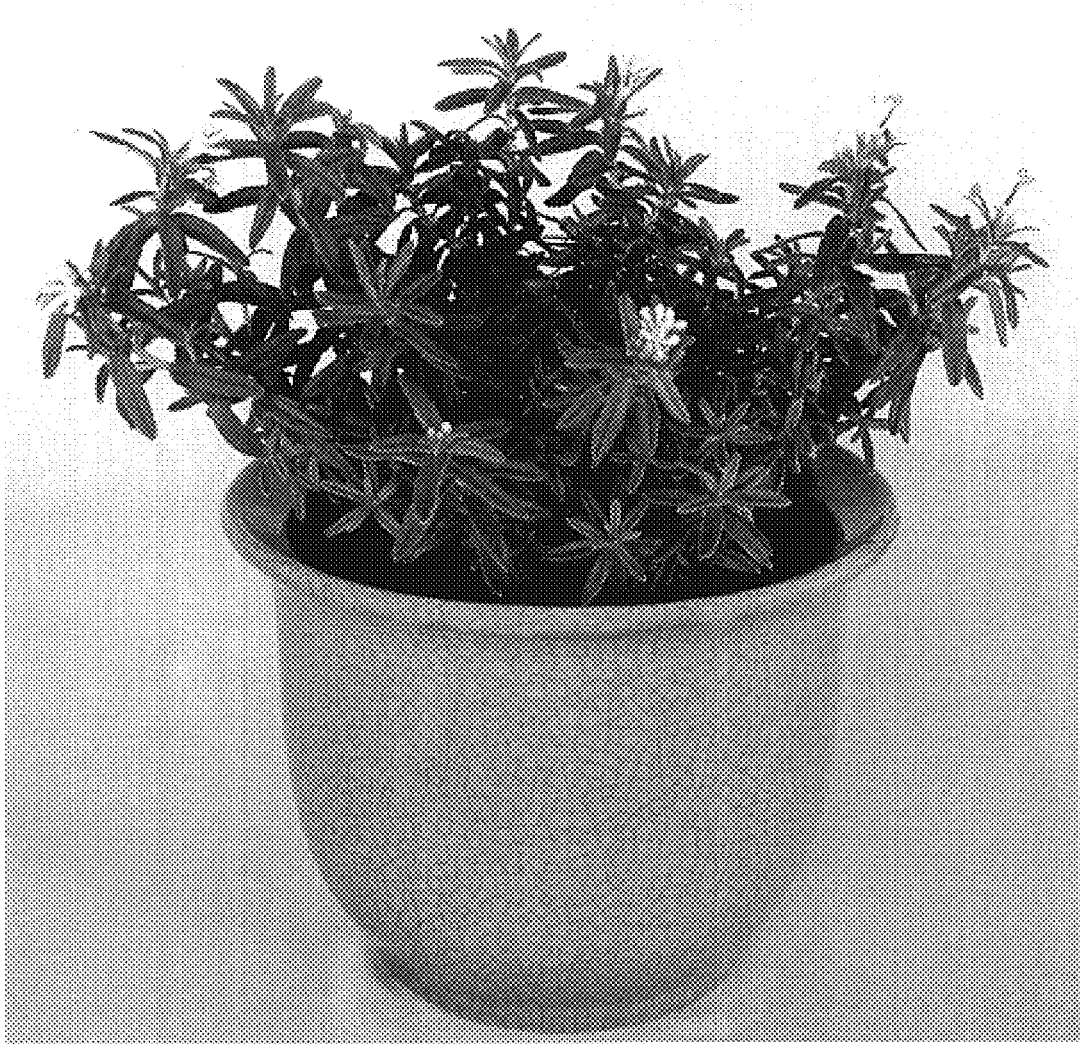

* * * * *